US008643675B2

(12) United States Patent
Mlejnek et al.

(10) Patent No.: US 8,643,675 B2
(45) Date of Patent: Feb. 4, 2014

(54) METHOD AND A SYSTEM FOR INTERACTIVE PROBING AND ANNOTATING MEDICAL IMAGES USING PROFILE FLAGS

(75) Inventors: Matej Mlejnek, Vienna (AT); Eduard Groller, Vienna (AT); Anna Vilanova, Eindhoven (NL)

(73) Assignee: Koninklijke Philips N.V., Eindhoven (NL)

(*) Notice: Subject to any disclaimer, the term of this patent is extended or adjusted under 35 U.S.C. 154(b) by 1301 days.

(21) Appl. No.: 12/090,894

(22) PCT Filed: Oct. 18, 2006

(86) PCT No.: PCT/IB2006/053841
§ 371 (c)(1),
(2), (4) Date: Apr. 21, 2008

(87) PCT Pub. No.: WO2007/046063
PCT Pub. Date: Apr. 26, 2007

(65) Prior Publication Data
US 2008/0300482 A1    Dec. 4, 2008

(30) Foreign Application Priority Data

Oct. 21, 2005   (EP) ..................................... 05109844

(51) Int. Cl.
*G06T 19/00*   (2011.01)
(52) U.S. Cl.
USPC .......................................... 345/632; 345/633

(58) Field of Classification Search
CPC ........................... G06T 19/006; G06T 2210/41
USPC ..................................................... 345/632, 633
See application file for complete search history.

(56) References Cited

U.S. PATENT DOCUMENTS 5,526,812 A     6/1996   Dumoulin et al.

FOREIGN PATENT DOCUMENTS

WO    WO03045222 A2    6/2003
WO    WO2004057439 A2    7/2004

OTHER PUBLICATIONS

Willem C. de Leeuw and Jarke J. van Wijk; A probe for local Flow Field Visualization; Oct. 25-29, 1993; In Proceedings of IEEE Visualization 1993; pp. 39-45 and CP5.*
Matej Mlejnek, Pierre Ermes, Anna Vilanova, Rob van der Rijt, Harrie van den Bosch, Frans Gerritsen, Meister Eduard Gröllier; Profile Flags: a Novel Metaphor for Probing of T2 Maps; Oct. 23-28, 2005; In Proceedings of IEEE Visualization 2005, pp. 599-606.*

(Continued)

*Primary Examiner* — Jeffery A Brier

(57) ABSTRACT

A method (100) of and a system (800) for probing a data of interest on the basis of an object comprised in a related image data, includes an instantiating step (105) for instantiating a probe, an applying step (115) for applying the probe to a location on a surface of the object, and a determining step (120) for determining a profile from the data of interest on the basis of the location of the probe. The probe is a virtual tool for extracting information from the data of interest. This tool is navigated on the basis of a view rendered from the related image data. The probe further determines the scope of probing. Thus, the method (100) and the system (800) enable the user to extract the desired information from the data of interest.

20 Claims, 9 Drawing Sheets

(56) References Cited

OTHER PUBLICATIONS

Matej Mlejnek, Pierre Ermes, Anna Vilanova, Rob van der Rijt, Harrie van den Bosch, Frans Gerritsen, M. Eduard Gröllier; Application-Oriented Extensions of Profile Flags; 2006; In Proceedings of the Eighth Joint Eurographics/IEEE VGTC conference on Visualization, Eurographics Association, pp. 339-346.*

Matej Mlejnek; Medical Visualization for Orthopedic Applications; May 2006; Tuwien, Techische Universitat Wien, Vienna University of Technology, Dissertation, pp. 1-91.*

Koehl et al: "A PACS-Based Interface for 3D Anatomical Structures Visualization and Surgical Planning"; Medical Imaging 2002: Visualization, Image-Guided Procedures, and Display, Feb. 24-26, 2002, San Diego, CA, Proceedings of SPIE vol. 4681, pp. 17-24.

Mosher et al: "Human Articular Cartilage: Influence of Aging and Early Symptomatic Degeneration on the Spatial Variation of T2-Preliminary Findings at 3 T1."; Radiology, Jan. 2000, vol. 214, pp. 259-266.

Belleman et al: "GEOPROVE: Geometric Probes for Virtual Environments"; High-Performance Computing and Networking. 7th International Conference, HCPN Europe 1999. Proceedings Springer-Verlag, Berlin Germany, pp. 817-827.

Preim et al: "Integration of Measurement Tools in Medical 3D Visualizations"; IEEE Conference on Visualization 2002, Oct. 27, 2002, pp. 21-28.

* cited by examiner

METHOD AND A SYSTEM FOR INTERACTIVE PROBING AND ANNOTATING MEDICAL IMAGES USING PROFILE FLAGS

This invention relates to a method of probing a data of interest on the basis of an object comprised in a related image data.

The invention further relates to a system for probing a data of interest on the basis of an object comprised in a related image data.

The invention further relates to an acquisition apparatus for acquiring an image data comprising said system.

The invention further relates to a workstation comprising said system.

The invention further relates to a computer program comprising program code means for performing said method.

The invention further relates to a computer program product comprising program code means stored on a computer readable medium for performing said method when said program product is run on a computer.

An embodiment of the method of the kind described in the opening paragraph is described in the article "Integration of Measurement Tools in Medical 3d Visualizations" by Bernhard Preim, Christian Tietjen, Wolf Spindler, and Heinz-Otto Peitgen, published in Proceedings of IEEE Visualization 2002, pages 21-28, 2002. This article describes tools, such as a distance line and angle measurement tools, for interactive and for automatic 3D measurements of viewed objects. Segmentation information may be exploited to enhance measurements by providing support for determining object diameters and angles between objects. This method is, however, suitable for and limited to extracting geometrical information about objects represented in a view rendered from an image data. On the other hand, there is a lot of further information comprised in the image data as well as in a data of interest related to the image data such as a data acquired using a data acquisition apparatus different from that used to acquire the image data. For example, it may be of interest to a physician to visualize local density across a femur bone, which local density can be derived from the intensities of a Volumetric Computed Tomography (CT) image data. Another example is a $T_2$ magnetic resonance (MR) relaxation-time map representing the tissue quality in the articular cartilage covering surfaces of knee joints. Thus, there is a need for a tool that allows probing a data of interest on the basis of an object comprised in a related image data and represented in a view rendered from the related image data.

It is an object of the invention to provide a method of the kind described in the opening paragraph, which is suitable for extracting useful information from a data of interest on the basis of an object in a related image data.

This object of the invention is achieved in that the method of probing a data of interest on the basis of an object comprised in a related image data comprises:

an instantiating step for instantiating a probe;

an applying step for applying the probe to a location on a surface of the object; and a determining step for determining a profile from the data of interest on the basis of the location of the probe.

The probe is a tool, which may be associated with the data of interest to be probed. The probe also comprises means for determining the scope of probing. The data of interest is stored as a scalar or a vector field, where locations from an image data related to the data of interest are assigned respective values of the field stored in the data of interest. The probe is instantiated and applied to a location on the surface of the object represented in a view rendered from the related image data. The object may be defined by segmenting the image data, prior to probing, and the image data may comprise segmentation results along with a field of image intensities or color codes. The view rendered from the related image data allows navigating the data of interest. The probe is a virtual measuring device such as a magnetic resonance spectrometer or a polarimeter, for example. The scope of the probe, i.e., a subdomain of the field representing the data of interest, is determined on the basis of the location of the probe. For example, the subdomain may comprise locations on an interval perpendicular to the surface of the object at the location of the application of the probe. The values of the field representing the data of interest, corresponding to the locations comprised in the subdomain, determine the profile such as a partial graph of said field. Thus, the method of the current invention is suitable for extracting useful information from the data of interest on the basis of an object in a related image data.

In an embodiment of the method according to the invention, the method comprises a setting step for setting a parameter of the probe. The parameter may define the scope of the probe, i.e., a subdomain of the field representing the data of interest. Optionally the parameter may define a type of the profile. For example, the parameter may indicate that the profile comprises a raw data of interest, a directional derivative of the data of interest, or a local average of the data of interest. Optionally, a parameter of the probe may assume a default value, which may be modified in the setting step. Alternatively, the parameter of the probe can be predefined and fixed.

In a further embodiment of the method according to the invention, the parameter defines a direction of the probe, a depth of the probe, and/or a range of the probe. The direction of the probe, the depth of the probe, and/or the range of the probe provide an advantageous way for determining the scope of the probe.

In a further embodiment of the method according to the invention, the method further comprises a visualizing step for visualizing the profile. The user can view and analyze the visualized profile. This profile may be displayed in a separate window outside the view rendered from the related image data or may be intelligently displayed within this view.

In a further embodiment of the method according to the invention, the probe comprises a flag for visualizing the profile. The flag comprising the profile is displayed in the view rendered form the related image data. A flagpole may also be used, for example, to indicate the direction of the probe and/or the location on the surface of the object at which the probe is applied.

In a further embodiment of the method according to the invention, the probe comprises a cutting plane for visualizing a cross section of the data of interest. In one implementation, the cutting plane is substantially perpendicular to the surface of the object at the location of application of the probe. The cutting plane defines a cross-section of the object. The cross-section comprises grayscale-coded or color-coded multiple profiles from the data of interest. Optionally, the cutting plane may rotate about an axis of the probe.

In a further embodiment of the method according to the invention, the method further comprises a browsing step for browsing the data of interest. To avoid to many instances of the probe, which could obscure the view rendered from the related image data, the method comprises a browsing step for changing the location of the probe on the surface of the object. At each chosen location of the probe the respective profile may be viewed.

In a further embodiment of the method according to the invention, the method further comprises a referencing step for setting up a reference profile from the data of interest. A reference probe may be instantiated and applied to a location on the surface of the object for determining a reference profile while another probe may be used for browsing the data of interest. The reference probe allows comparing profiles corresponding to different locations of the probe on the surface of the object.

In a further embodiment of the method according to the invention, the profile is determined on the basis of the reference profile within the determining step. The profile may be, for example, a difference profile representing the difference between the profile determined on the basis of the selected location of the probe and the reference profile.

In a further embodiment of the method according to the invention, the method further comprises an annotating step for annotating a view rendered from the related image data with the profile. This may be the final step of probing. The profiles annotating the view rendered from the related image data at selected locations of the probe on the surface of the object may be stored for future reference.

It is a further object of the invention to provide a system of the kind described in the opening paragraph that is suitable for extracting useful information from a data of interest on the basis of an object in a related image data. This is achieved in that the system for probing a data of interest on the basis of an object comprised in a related image data comprises:

- an instantiating unit for instantiating a probe;
- an applying unit for applying the probe to a location on a surface of the object; and
- a determining unit for determining a profile from the data of interest on the basis of the location of the probe.

It is a further object of the invention to provide an image acquisition apparatus of the kind described in the opening paragraph that is suitable for extracting useful information from a data of interest on the basis of an object in a related image data. This is achieved in that the image acquisition apparatus comprises a system for probing a data of interest on the basis of an object comprised in a related image data, the system comprising:

- an instantiating unit for instantiating a probe;
- an applying unit for applying the probe to a location on a surface of the object; and
- a determining unit for determining a profile from the data of interest on the basis of the location of the probe.

It is a further object of the invention to provide a workstation of the kind described in the opening paragraph that is suitable for extracting useful information from a data of interest on the basis of an object in a related image data. This is achieved in that the workstation comprises a system for probing a data of interest on the basis of an object comprised in a related image data, the system comprising:

- an instantiating unit for instantiating a probe;
- an applying unit for applying the probe to a location on a surface of the object; and
- a determining unit for determining a profile from the data of interest on the basis of the location of the probe.

It is a further object of the invention to provide a computer program of the kind described in the opening paragraph that is suitable for extracting useful information from a data of interest on the basis of an object in a related image data. This is achieved in that the computer program, when said program is run on a computer, comprises program code means for performing the following tasks of:

- instantiating a probe;
- applying the probe to a location on a surface of the object; and
- determining a profile from the data of interest on the basis of the location of the probe.

It is a further object of the invention to provide a computer program product of the kind described in the opening paragraph that is suitable for extracting useful information from a data of interest on the basis of an object in a related image data. This is achieved in that the computer program product comprises program code means stored on a computer readable medium for performing the following tasks when said program product is run on a computer:

- instantiating a probe;
- applying the probe to a location on a surface of the object; and
- determining a profile from the data of interest on the basis of the location of the probe.

Modifications and variations thereof, of the system, of the image acquisition apparatus, of the workstation, of the computer program, and/or of the computer program product, which correspond to modifications of the method and variations thereof, being described, can be carried out by a skilled person on the basis of the present description.

The method of the present invention is especially useful for probing a data of interest on the basis of an object comprised in a related 3D image data. However, this method can be also used for probing a data of interest on the basis of an object comprised in a related 2D image data and 4D image data. The modification of the method, of the system, of the image acquisition apparatus, of the workstation, of the computer program, and/or of the computer program product being obvious to a skilled person can be carried out on the basis of the description of the current invention. The image data can be routinely generated nowadays by various data acquisition modalities such as, but not limited to, Magnetic Resonance Imaging (MRI), Computed Tomography (CT), Ultrasound (US), Positron Emission Tomography (PET), and Single Photon Emission Computed Tomography (SPECT).

These and other aspects of the method, of the system, of the image acquisition apparatus, of the workstation, of the computer program, and of the computer program product according to the invention will become apparent from and will be elucidated with respect to the implementations and embodiments described hereinafter and with reference to the accompanying drawings, wherein:

FIG. 1 shows a flowchart of an exemplary embodiment of the method;

FIG. 2 schematically shows instantiating an exemplary probe;

FIG. 3 schematically shows components of an exemplary probe;

FIG. 4 schematically shows mapping of a needle into an axis of a profile;

FIG. 5 schematically shows exemplary flags with profiles;

Figure 8:
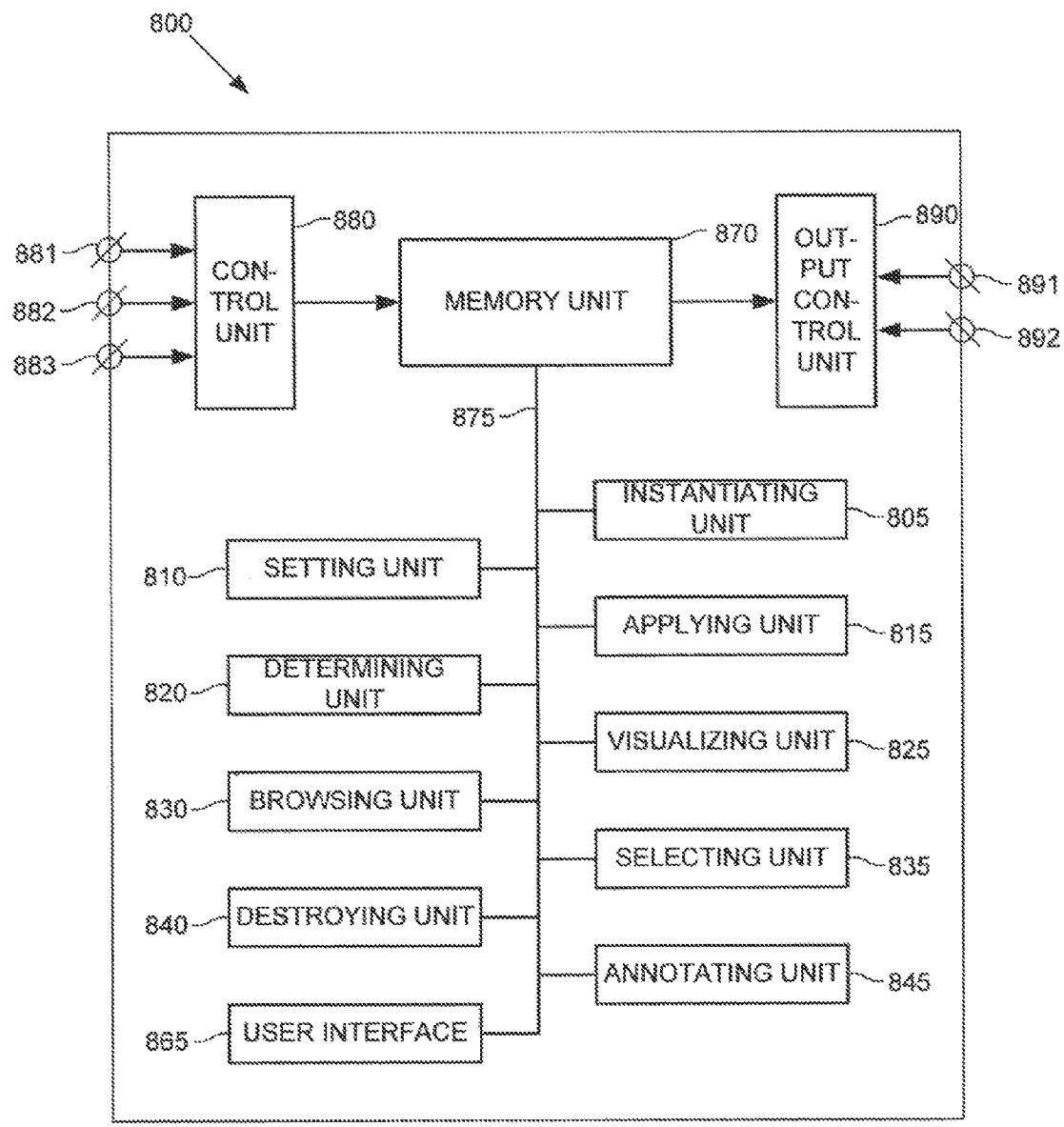
Figure 9:
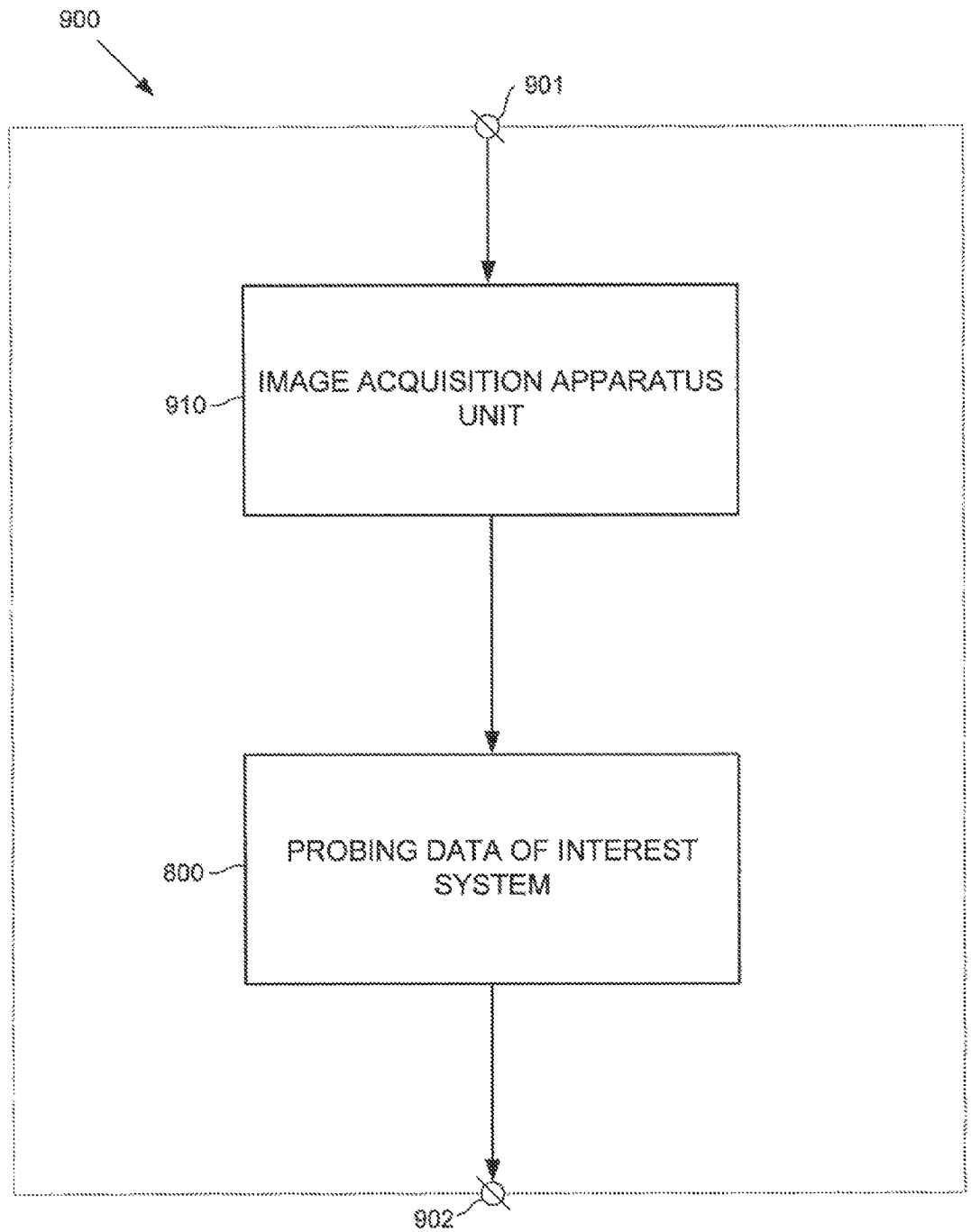
Figure 10:
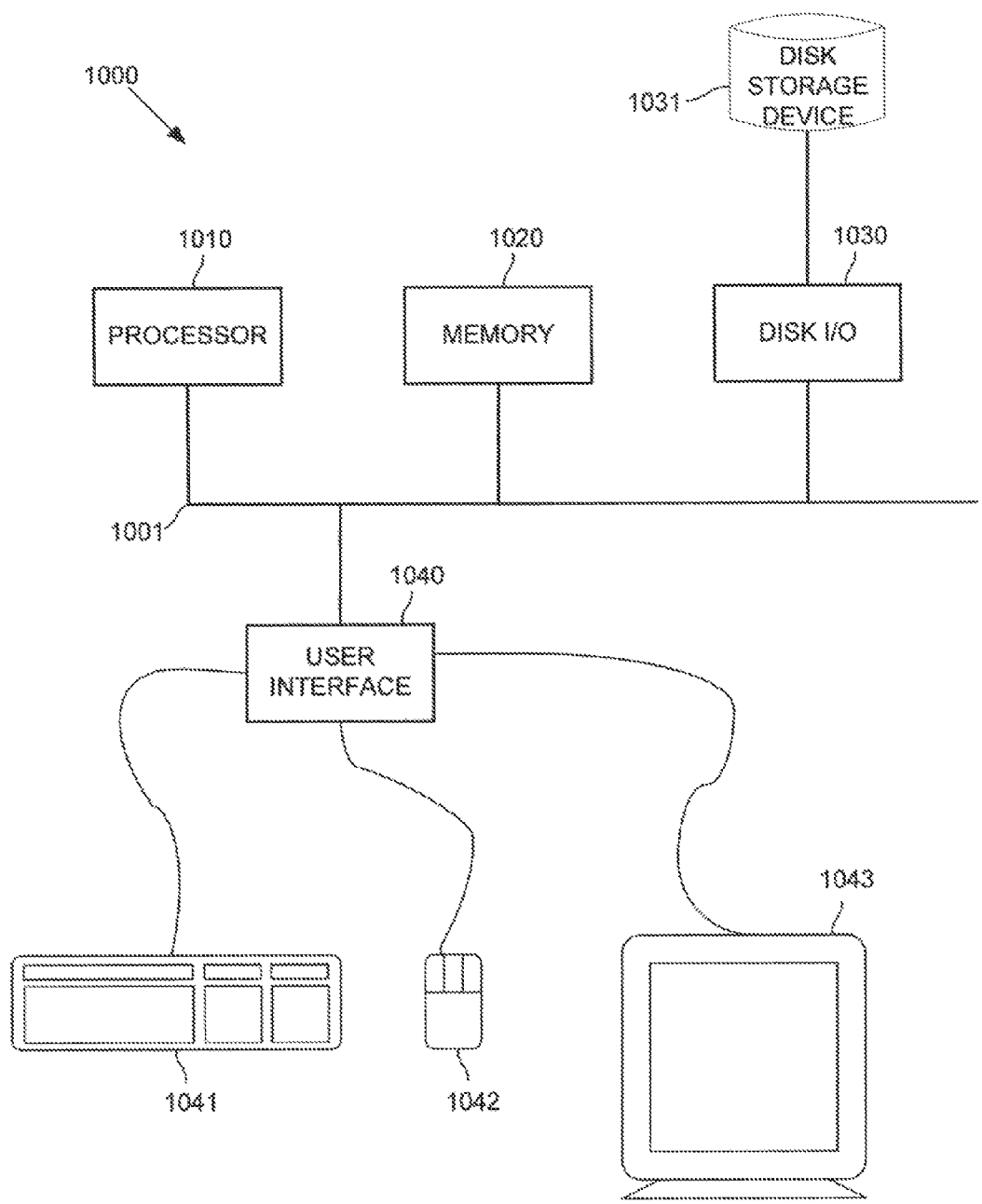

FIG. 8 schematically shows an embodiment of the system;

FIG. 9 schematically shows an embodiment of the image acquisition apparatus; and FIG. 10 schematically shows an embodiment of a workstation.

Same reference numerals are used to denote similar parts throughout the figures.

Figure 1:
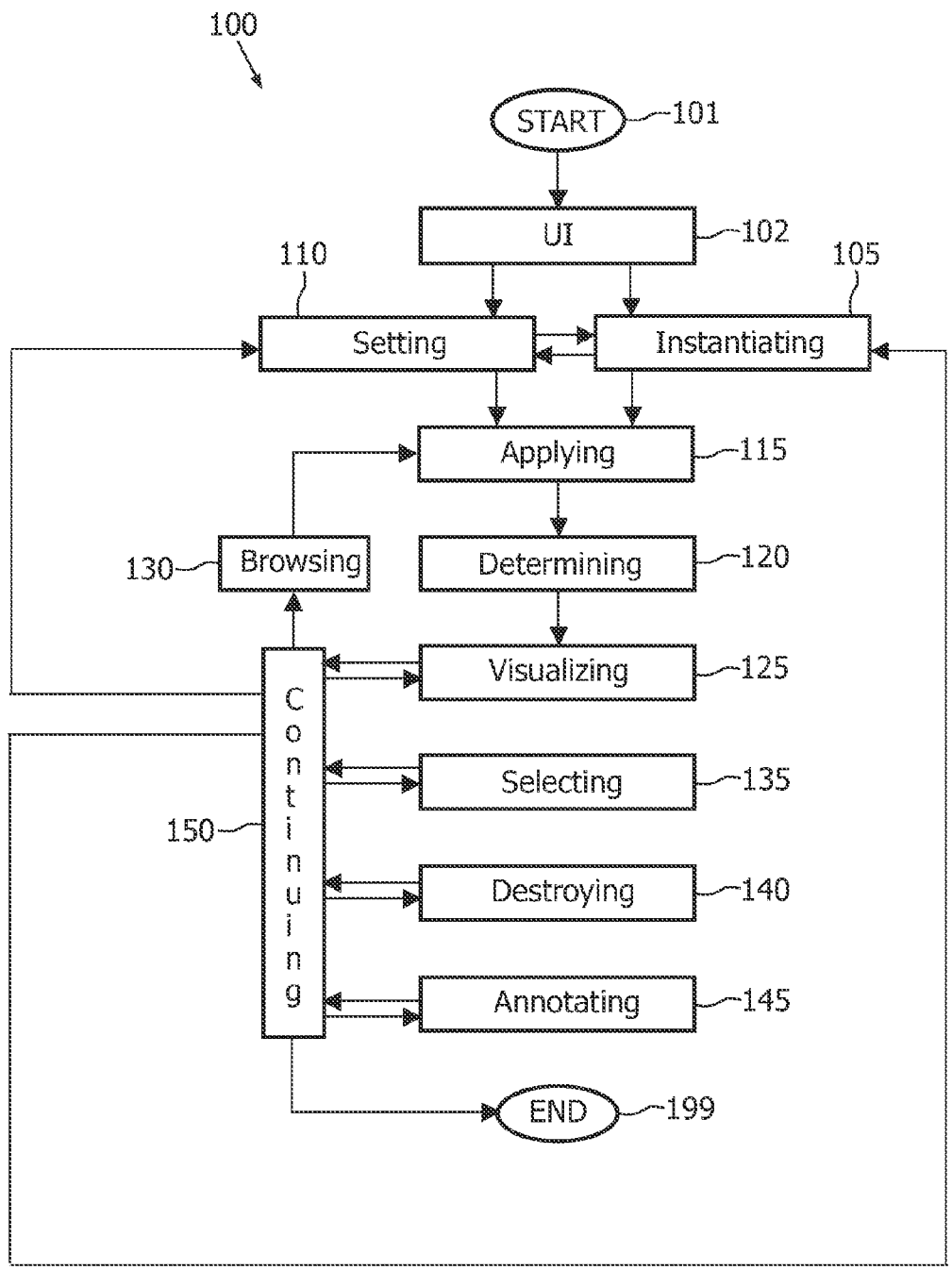

FIG. 1 shows a flowchart of an exemplary embodiment of the method 100 of the current invention. After a start step 101 the method 100 continues to a User Interface (UI) step 102 for displaying a user interface for communicating with a user. From there the method 100 may continue to an instantiating step 105 for instantiating a probe or to a setting step 110 for setting a parameter of the probe. The parameters of the probe may be set before or after instantiating the probe. The parameters of the probe may be further modified. The probe is applied to the surface of the object comprised in the related image data using the UI in an applying step 115. In a determining step 120 the profile from the data of interest is determined. This profile is visualized in a visualizing step 125. After the visualizing step 125 the method 100 continues to a continuing step 150. In the continuing step 150 the next step of the method 100 is determined. The next step may be any one of the instantiating step 105, the setting step 110, the browsing step 130, the selecting step 135, the destroying step 140, the annotating step 145, and the end step 199. The next step may be selected by the user. Optionally there may be a default next step.

In a browsing step 130 the probe may be translated on the surface of the object to a new location. After the browsing step 130 the method 100 continues to the applying step 115, then to the determining step 120 and to the visualizing step 125. After the visualizing step 125 the method 100 continues to the aforementioned continuing step 150. In a selecting step 135 a probe is selected. Setting a parameter of the probe in the setting step 110, moving the probe in the browsing step 130, and destroying the probe in the destroying step applies to the currently selected probe. After the selecting step 135 the method 100 continues to the aforementioned continuing step 150. In a destroying step 140 the probe selected by the user in the selecting step 135 is destroyed. After the destroying step 140 the method 100 continues to the aforementioned continuing step 150. In an annotating step 145, the image is annotated with the profile, i.e. the profile and the parameters of the probe are saved for future reference. After the annotating step 145 the method 100 further continues to the aforementioned continuing step 150. The method 100 terminates with an end step 199.

In an embodiment of the method 100 according to the invention, the UI may be a Graphical User Interface (GUI). The instantiating step 105, the setting step 110, the browsing step 130, the selecting step 135, the destroying step 140, the annotating step 145, and the end step 199 may be selected at any time and in any order using the UI. However, the browsing step 130 and the destroying step 140 will have an effect when at least one probe is selected. Similarly, the setting step 110 allows setting a parameter of a selected probe. If no probe is selected, the parameter set in the setting step 110 is applied to a probe instantiated in the instantiation step 105. The skilled person will understand that the UI may have many other means for determining the flow and parameters of the method 100. Some of the means are described in the description of the embodiments of the method 100 of the current invention. The UI may also comprise means for manipulating the view and/or the object in the view rendered from the related image data.

Figure 2:
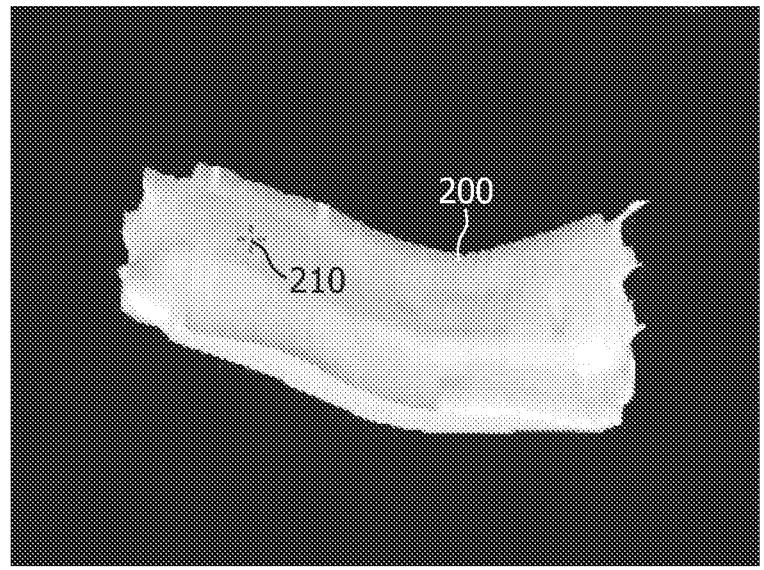
Figure 2:
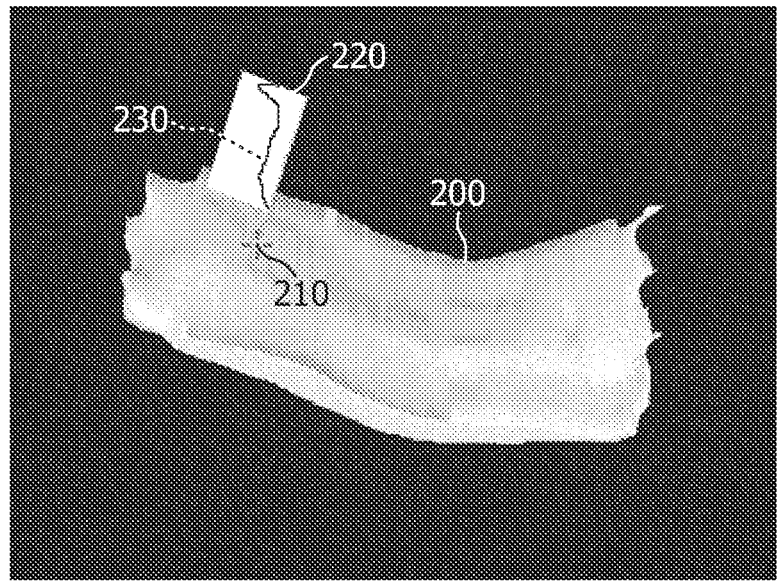

In the instantiating step 105 of the method 100 according to the invention, a probe for determining a profile from the data of interest is instantiated. FIG. 2 schematically shows instantiating an exemplary probe. The first image 201 shows the surface 200 of an object, the articular surface 200 of the knee cartilage reconstructed from anatomical scan MR data, and a pointer 210 operated using a user input device such as, but not limited to, a mouse or a trackball. At a location on the surface 200 of the cartilage the user may press a button of the mouse or of the trackball. As a result, the probe 220 is instantiated at this location as shown in the second image 202. The probe 220 visualizes a profile 230 from the data of interest determined on the basis of the location of the probe on the surface 200 in the view 202 rendered from the related image data. If desired, there may be multiple probes instantiated at different locations on the surface 200 of the cartilage. Optionally, the instantiated probe may automatically become the selected probe as if it were selected in the selecting step 135.

In an embodiment of the method 100 according to the invention, the method 100 comprises a setting step 110 for setting a parameter of the probe. Preferably the parameter of the probe is set to a default value when the probe is instantiated. The default value may be modified by the user in the setting step 110. An instantiated probe or a plurality of instantiated probes may be selected in the selecting step 135. The parameters set in the setting step 110 apply to the selected probe or to the plurality of selected probes, respectively. Optionally, if no probe is selected, a new default parameter may be set in the setting step 110. The parameter may define the scope of the probe, i.e., a subdomain of the field representing the data of interest. Another parameter of the probe may define the type of the profile. For example, the parameter may indicate that the profile comprises a raw data of interest, a directional derivative of the data of interest, or a local average of the data of interest. Also, the parameter may define how the profiles are going to be displayed and/or how many profiles are going to be displayed.

The parameter of the probe may be set using a window of a UI for setting a parameter of the probe. This window may comprise text boxes, lists, buttons, and similar gadgets known to the skilled person. Optionally, a parameter may be set using a graphical representation of the probe.

The skilled person will appreciate that there are many parameters that can be used to make the method 100 effective and that the parameters used in this description are for illustration and must not be interpreted as limiting the scope of the invention.

In a further embodiment of the method 100 according to the invention, the parameter defines a direction of the probe, a depth of the probe, and/or a range of the probe. The direction of the probe, the depth of the probe, and/or the range of the probe provide an advantageous way for determining the scope of the probe. The parameters may be set using the aforementioned dedicated window of the UI before and/or after instantiating the probe and may be modified after instantiating the probe. Alternatively, the user may be able to manipulate a representation of the probe using a user input device such as, but not limited to, a mouse or a trackball. The latter case is illustrated by the following example.

Figure 3:
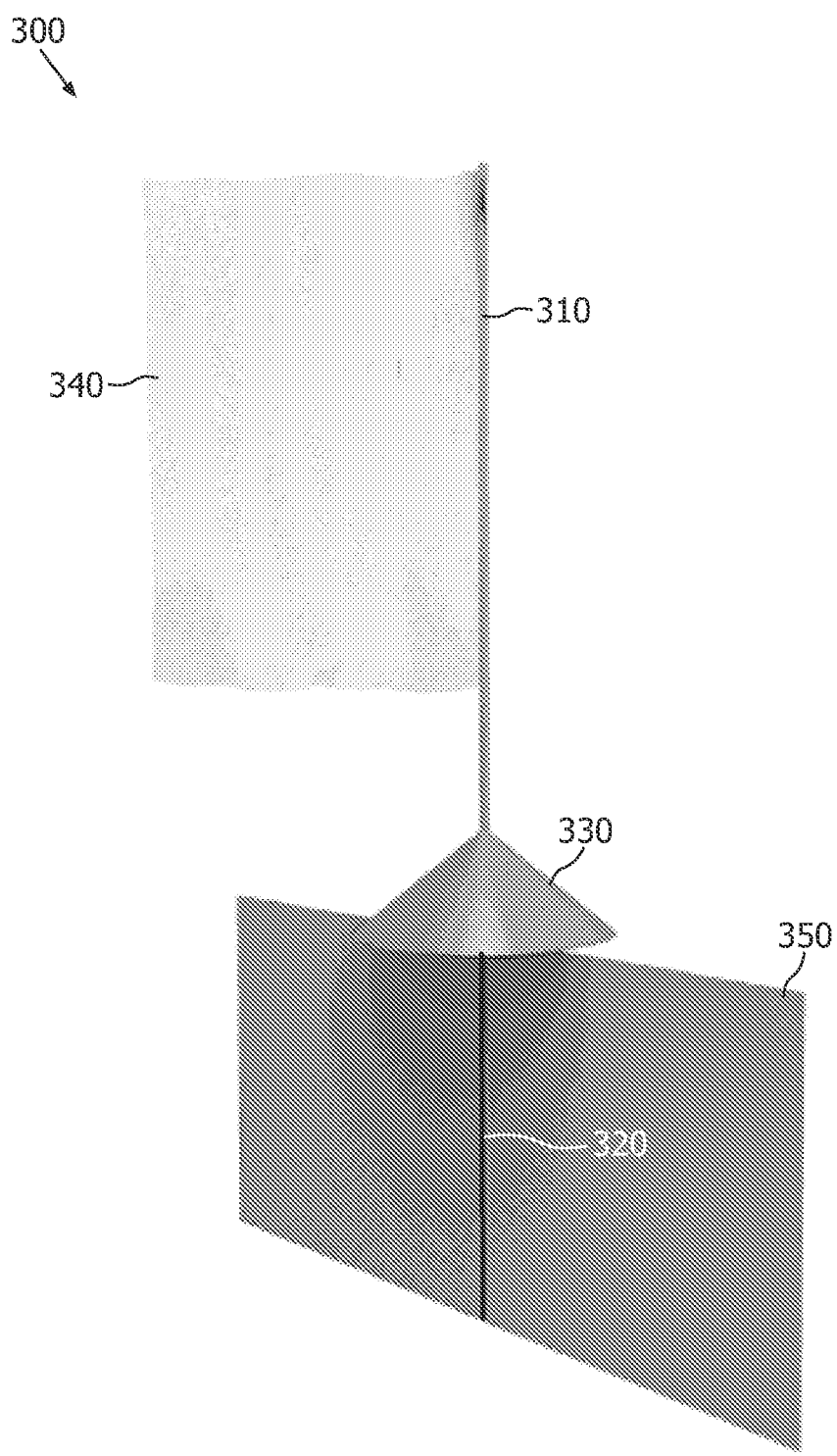

FIG. 3 schematically shows components of an exemplary probe 300, which can be employed by the method 100. The components of the probe 300 may be also arranged for setting a direction of the probe, a depth of the probe, a range of the probe, and/or another parameter. The probe 300 comprises a flagpole 310, a needle 320, a cone 330, a flag 340, and a cutting plane 350. When a probe 300 is applied to a location on the surface of an object, the flagpole 310, the cone 330, and the flag 340 are visible. The needle 320 and/or the cutting plane 350 may be shown only for setting a parameter of the probe or may be not shown at all. A parameter of the probe 300 may be defined, for example, using a text box, a list, or a button in a dedicated window of the UI. Alternatively, a parameter of the probe 300 may be defined by manipulating the probe 300 using a user input device such as, but not limited to, a mouse or a trackball. Defining a parameter of the probe 300 may take place before and/or after instantiating the probe 300.

The flagpole 310 is an exemplary embodiment of the direction selector for setting the direction of probing. The user may set the direction of the flagpole 310 by rotating the flagpole 310 around the bottom end of the flagpole 310, using a user input devices such as, but not limited to, a mouse or a trackball. The default direction of the flagpole 310 of a newly instantiated probe applied to the surface of the object may be substantially perpendicular to that surface. Alternatively, the direction of the flagpole 310 may be fixed in a predefined direction, e.g., in a direction substantially perpendicular to the surface of the object.

The needle 320 is an exemplary embodiment of the depth selector for setting the depth of probing. The needle 320 is an extension of the flagpole 310 and is aligned with the flagpole 310. Therefore, the needle also defines the direction of probing. Thus, the needle 320 may be used for setting the direction of the probe. First of all, however, the needle is used to set the depth of probing. The depth of probing is defined by the length of the needle 320. The length of the needle 320 may be set by inputting a numerical value of the length in a UI window for setting parameters of the probe. Alternatively, using a user input device such as, but not limited to, a mouse or a trackball, the user may adjust the length of the needle 320 by pulling the tip of the needle. This kind of needle 320 is referred to as an absolute needle. Alternatively, a parameter of the needle 320 may be set to define an adaptive needle. An adaptive needle adapts the depth of probing to the object, to the location of the probe 300 on the surface of the object, and to the direction of the probe 300. For example, an adaptive needle may probe the data of interest in locations corresponding to the locations comprised along the needle extending between a first surface and a second surface of the object such as the articular surface and the subchondral surface of the knee cartilage. When the probe 300 is applied to the surface of the object, the needle 320 is not visible, hidden underneath the surface of the object. However, during the setting step 110 the needle 320 may be made visible for setting the depth of probing.

The cone 330 is an exemplary embodiment of the range selector for setting the range of probing. The range selector enables setting of the size of the probed neighborhood. The cone axis is aligned with the axis of the probe 300 defined by the flagpole 310 and by the needle 320. The radius of the cone 330 may be set using a UI window for setting a parameter of the probe 300. Alternatively, the radius of the cone 330 may be set by dragging the base of the cone using a mouse or a trackball. The base of the cone defines a cylinder. The axis of the cylinder is substantially identical with the axis of the probe. The cylinder comprises a plurality of needles, each needle being substantially parallel to the axis of the cylinder. The number of needles may be determined automatically or may be set by the user in the setting step 110. The needles may be absolute needles. In this case all needles have the same length. Alternatively the needles may be adaptive needles. One end of every needle, whether absolute or adaptive, is located on a first surface of the object. In case of adaptive needles, the other end of every needle may be located on a second surface of the object.

The method 100 is further arranged to determine a profile corresponding to locations along a needle comprised in the cylinder. A plurality of profiles may be determined, each profile corresponding to one needle. Alternatively, the upper and lower envelope profiles, as described later in the description of the current invention, of the plurality of profiles may be determined. If the radius of the cone is zero, only one profile corresponding to locations on the needle 320 is determined.

The flag 340 and the cutting plane 350 are used for visualizing the determined profiles and will be described in more detail later. The dimensions of the flag correspond to the length of the needle and to the range of values determined from the data of interest. The flag 340 and the cutting plane 350 are arranged to facilitate visualizing a profile extracted from the data of interest.

It is understood that the skilled person will know many ways how to manipulate the flagpole 310, the needle 320, and the cone 330, for example, using a pointer controlled by a user input device such as mouse, a trackball, a keyboard, or using a text box for entering a numerical value of a parameter of the probe 300. The ways described in the description of the embodiments of the method 100 of the current invention illustrate rather than limit the invention.

The skilled person will understand that there may be other implementations of the probe useful for performing the steps of the method 100 of the current invention and that the implementation of the probe 300 described above is for illustrating the embodiments of the current invention and does not limit the scope of the claims.

In the applying step 115 of the method 100 according to the invention, the probe is applied to a location on a surface of the object. The location of the probe may be defined in the instantiating step 105 or in the browsing step 130. The coordinates of the location on the surface of the object where the probe has been placed are computed. These coordinates, together with the definition of the scope of the probe are used in the determining step 120 to determine a profile or multiple profiles from the data of interest.

In the determining step 120 a profile from the data of interest is determined on the basis of the location of the probe and of the scope of the probe. The location of the probe may be defined in the instantiating step 105 or in the browsing step 130 and the scope of the probe may be defined in the setting step 110. Determining the data of interest may involve any of the sampling techniques such as interpolating and/or extrapolating the missing data. Useful smoothing filters may also be used. In addition, determining the profile may also involve transforming the data of interest. A useful transformation may be set in the setting step 110. Alternatively, the transformation may be predefined.

The data of interest may be any data related to the location on the surface of the object in a view rendered from the related image data, to which the probe is applied. Typically, the data of interest is a field assigning values such as scalar or vector values, to spatial locations. For example, the data of interest may be a MR $T_2$ relaxation time map calculated from a sequence of single-echo images related to an image data obtained from the anatomical MR scan. Other examples comprise, but are not limited to, dielectric polarizability, magnetic susceptibility, local density, local concentration of an element or of a chemical compound, and Hounsfield values. In a particular case, the data of interest may be the image data itself. The related image data, on the other hand, may be nowadays routinely generated by the data acquisition modalities comprising, but not limited to, MRI, CT, US, PET, and SPECT.

In a further embodiment of the method 100 according to the invention, the method further comprises a visualizing step 125 for visualizing the profile. The visualizing step 125 allows viewing and analyzing the profile. The profile may be displayed in a separate window outside the view rendered from the related image data and/or may be intelligently displayed within this view, for example in the flag area of the probe 300 or in a cross-section of the object displayed in the view rendered from the related image data. The second option is particularly advantageous because that option allows easily and quickly associating the data of interest with the location on the surface of the object comprised in the related image data and displayed in a view rendered from the related image data. The visualization mode may be defined by a parameter of the method 100 settable in the setting step 110 or may be predefined.

In a further embodiment of the method 100 according to the invention, the probe 300 comprises a flag 340 for visualizing the profile. The flag 340 provides an area for visualizing the profile determined from the data of interest. Locations on the needle 320 are mapped onto a first axis of the profile. Values from the data of interest are mapped on a second axis of the profile. The first axis of the profile may be substantially parallel to the flagpole 310. The second axis of the profile may be substantially perpendicular to the flagpole 310. The direction of the flagpole and the bottom end of the flagpole 310 advantageously indicate the location of the probe 300 for determining the profile from the data of interest. An exemplary profile 230 is shown in image 202 in FIG. 2. Visualizing the first axis and the second axis is optional. In the image 202 the axes are not visualized.

Figure 4:
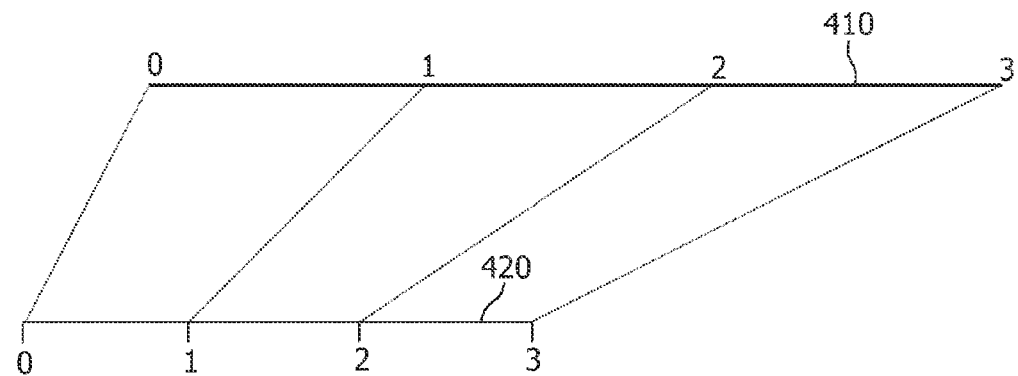
Figure 4:
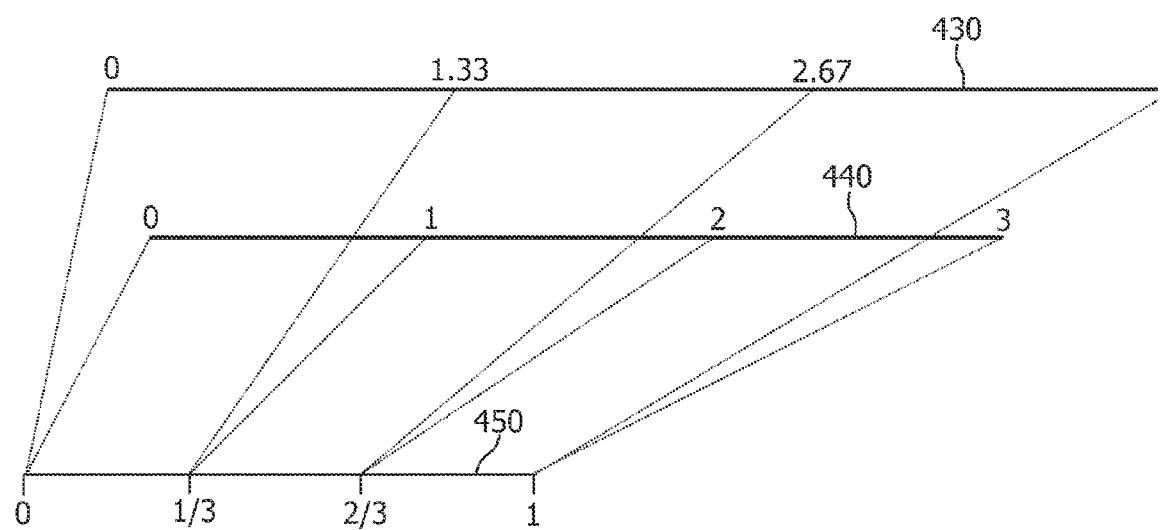

There are various types of flags differing in contents and in the way the flag contents is visualized. One type of the flag, for example, corresponds to the type of the needle. This is illustrated in FIG. 4 schematically showing mapping of a needle into an axis of a profile. An absolute needle 410 is mapped into the interval of the first axis 420. Each interval of the absolute needle is scaled and represented by an interval on the first axis. The ratio of the length of an interval of the first axis 420 and of the length of a respective interval of the absolute needle 410 is constant and independent of the location of the probe comprising the absolute needle 410 or on the instance of the probe comprising the absolute needle 410.

With further reference to FIG. 4, a first adaptive needle 430 and a second adaptive needle 440 have different lengths. The adaptive needles 430 and 440 are mapped into the same normalized interval of the first axis 450 of length 1. The ratio of the lengths of two intervals of the first axis 450 is the same as the ratio of the lengths of two respective intervals of the adaptive needle 440 and the same as the ratio of the lengths of two respective intervals of the adaptive needle 450. Thus, this ratio is independent of the location of the probe comprising the adaptive needle 430 and/or the adaptive needle 440, or on the instance of the probe comprising the adaptive needle 430 and/or the adaptive needle 440.

Figure 5:
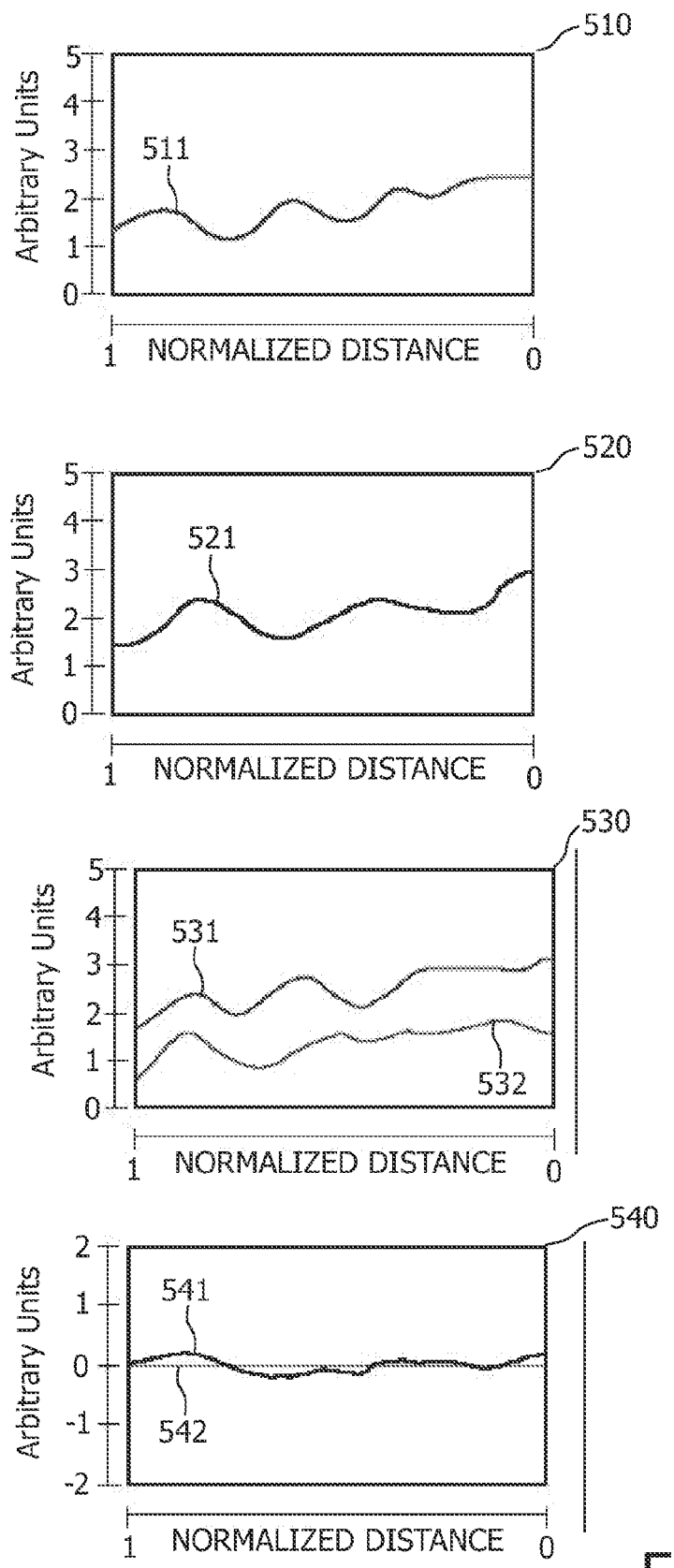

Another type of the flag corresponds to the contents of the flag. FIG. 5 schematically shows exemplary flags with normalized profiles. Flags classified according to the contents comprise, but are not limited to, a single profile flag 510, an average profile flag 520, a profile range flag 530, and a deviation flag 540. The single profile flag 510 comprises a single profile 511 corresponding to locations on the needle 320 of a probe 300. The average profile flag 520 comprises an average profile 521 of profiles $f_1, \ldots, f_n$ corresponding to locations on the needles comprised in a cylinder defined by the cone 330 of the probe 300. The average profile is defined at each location x on the normalized first axis as the average of the values of the profiles $f_1, \ldots, f_n$, at this location x, namely $f^{average}(x) = (1/n)[f_1(x) + \ldots + f_n(x)]$. The range flag 530 shows the upper envelope profile 531 and the lower envelope profile 532 determined on the basis of the profiles $f_1, \ldots, f_n$ corresponding to locations on the needles comprised in a cylinder defined by the cone 330 of the probe 300. The upper envelope of profiles $f_1, \ldots, f_n$ is a profile defined at each location x on the normalized first axis as the maximum of the values of the profiles $f_1, \ldots, f_n$, at this location x, namely $f^{upper}(x) = \max\{f_1(x), \ldots, f_n(x)\}$. The lower envelope of profiles $f_1, \ldots, f_n$ is a profile defined at each location x on the normalized first axis as the minimum of the values of the profiles $f_1, \ldots, f_n$, at this location x, namely $f^{lower}(X) = \min\{f_1(x), \ldots, f_n(x)\}$. The deviation profile flag 540 is essential for visualizing multiple profiles using multiple flags. One of the flags is designated as a reference flag. For example, the single profile 511 or the single average profile 521 comprised in the reference flag is a reference profile. A deviation flag 540 comprises the deviation profile 541 defined as the difference between the respective profile determined at the location of the probe comprising the deviation flag and the reference profile. The deviation flag 540 also comprises the zero line 542.

The skilled person will appreciate that there are many other useful types of flags and profiles that may be determined and may be visualized using the method 100 of the current invention. The flag types and profile types described above serve the purpose of illustrating embodiments of the invention and do not limit the scope of the claims.

In a further embodiment of the method 100 according to the invention, the probe 300 comprises a cutting plane 350 for visualizing a cross section of the data of interest. The cutting plane defines another way for visualizing the data of interest by probing the data with multiple substantially mutually parallel needles. The direction of probing is determined by the axis of the probe. The density of the parallel needles in the cutting plane may be a predefined parameter or may be set by the user. The cutting plane 350 is substantially perpendicular to the surface of the object at the location of application of the probe 300. Preferably, the cutting plane is substantially identical with a plane comprising the probe axis, and a line perpendicular to the viewing direction. Other choices of the cutting plane are also possible.

Figure 6:
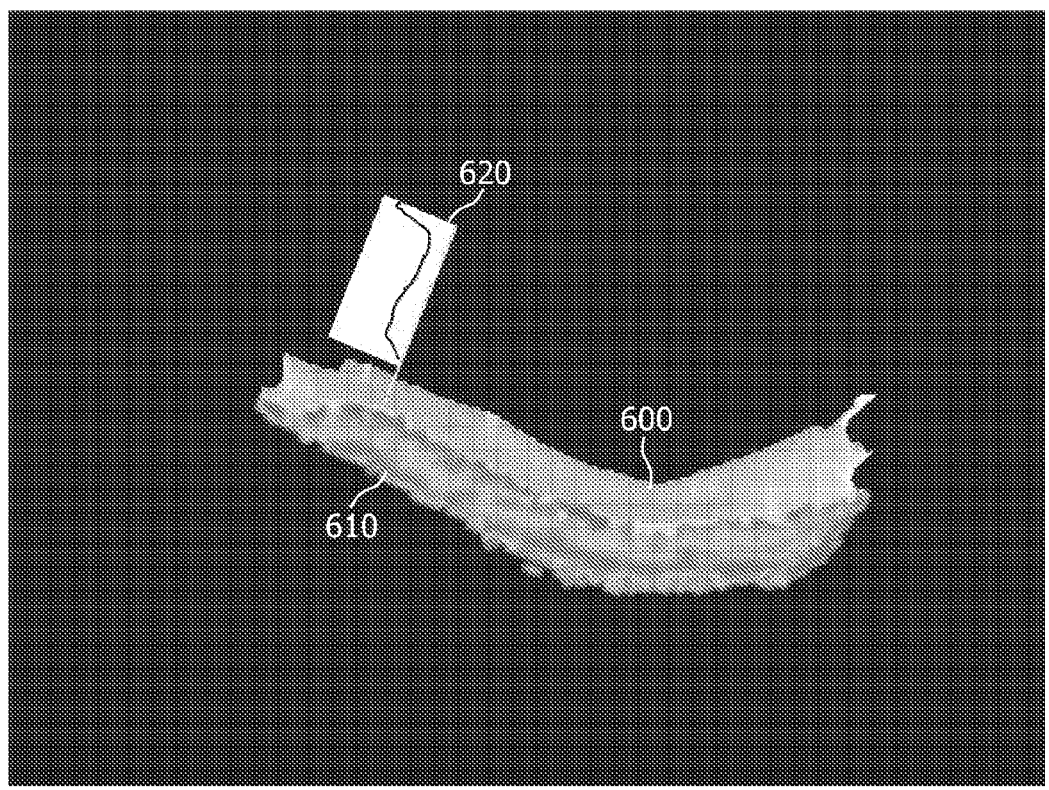
FIG. 6 shows an exemplary cross-section of a data of interest.

An exemplary cross-section of a data of interest by a cutting plane is shown in FIG. 6. Here MR $T_2$ relaxation time data is probed at locations distributed on the cross-section 610 of the knee cartilage 600 by the cutting plane of the probe 620. The structures in front of the cutting plane are removed from the rendered view of the related image data. The values of $T_2$ relaxation time from the data of interest may be color-coded or grayscale-coded. Thus, the cross-section 610 comprises color-coded or grayscale-coded multiple profiles from the data of interest.

In order to enable the investigation of a neighborhood of the profile corresponding to the locations on the probe axis, the cutting plane may rotate about an axis substantially identical with said probe axis. Alternatively, the whole object may rotate about an axis substantially identical with the probe axis. The needle is not rendered in order not to hide the cross-section profile along the needle, which may also be visualized in a single profile flag of the probe 620.

In a further embodiment of the method 100 according to the invention, the method further comprises a selecting step 135 for selecting and for deselecting a probe. The selected probe may be marked as selected. The ways of marking a selected object such as probe are known to the skilled person. The setting step 110, the browsing step 130, and the destroying step 140 may be applied to the selected probe. Multiple probes may be selected. The ways of selecting and deselecting a probe or multiple probes using a user input device such as, but not limited to, a mouse or a trackball, are known to the skilled person.

In a further embodiment of the method according to the invention, the method further comprises a browsing step 130 for browsing the data of interest. A probe may be selected for browsing by the user using an input device such as, but not limited to, a mouse or a trackball in the selecting step 135. Optionally, multiple probes may be selected for browsing. The selected probe may be translated on the surface of the viewed object to investigate profiles at different locations on the surface. Alternatively the object may be translated and rotated in space while the selected probe is at a fixed position in the view rendered from the related image data and the bottom end of the flagpole is on surface of the object. The profiles visualized in the flag may be updated periodically. After a predefined time period, the method continues from the browsing step 130 to the applying step 115. In the applying step 115, the current position of the probe is determined and the method 100 continues to the determining step 120. In the determining 120 step the profile or profiles corresponding to the location of the probe and to the settings of the probe are determined and the method continues to the visualizing step 125. In the visualizing step 125 the profile or profiles corresponding to the visualization mode are visualized. The skilled person will understand that there are alternative methods to implement the browsing step and that the method described in this embodiment is for illustration purposes only, and does not limit the scope of the claims. The browsing step 130 provides an advantageous way for choosing a desired location of the probe. The browsing step 130 also allows inspecting multiple profiles while avoiding too many instances of the probe, which could obscure the view rendered from the related image data.

Figure 7:
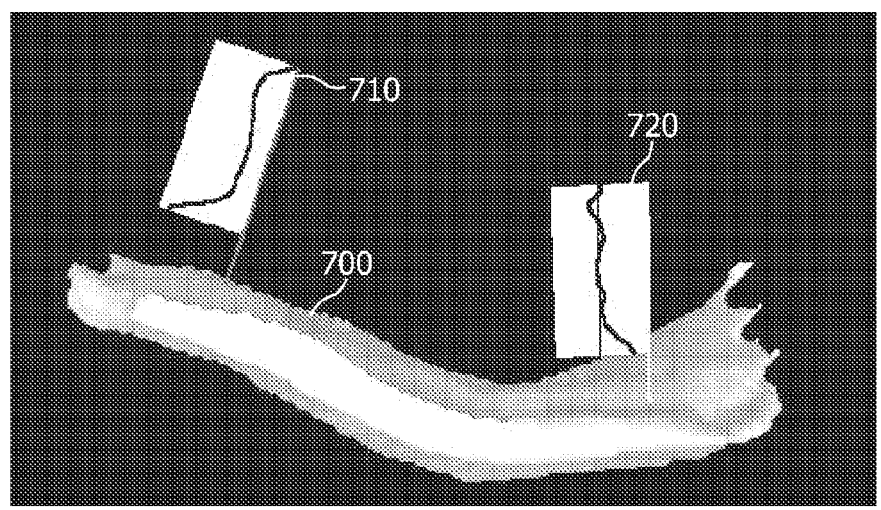
FIG. 7 shows an exemplary reference probe and another probe.

In a further embodiment of the method 100 according to the invention, the method further comprises a referencing step 110 for setting up a reference profile from the data of interest. FIG. 7 shows an exemplary reference probe 710 and another probe 720 applied to the surface 700 of the cartilage. A reference probe 710 may be instantiated in the instantiating step 105 and applied to a location on the surface 700 of the object for determining a reference profile. The type of the probe to be instantiated may be set to reference type in the setting step 110. Alternatively, an existing probe may be selected in the selecting step 135 and the type of the selected probe may be set in the setting step 110 as a reference probe type. In the preferred embodiment there may be at most one reference probe at any moment of time. Another probe 720 may be then used for browsing the data of interest and a profile visualized in this another probe 720 may be compared to the reference profile. The reference probe may be de-referenced in the setting step 110.

In a further embodiment of the method 100 according to the invention, the profile is determined on the basis of the reference profile within the determining step 120. For example the profile determined by another probe 720 may be a deviation profile such as the deviation profile 541 shown in FIG. 5. In a clinical application the reference probe may be located at a position showing a healthy $T_2$-profile. Additional probes are applied to visualize the deviation of profiles at their locations from the reference profile. The deviation of the local profile may be additionally depicted in a different color. Other ways for determining profiles are also contemplated. For example, a quotient profile may be determined by dividing each value of the profile by the respective value of the reference profile. In addition, a cross section may also visualize profiles determined on the basis of a reference profile, e.g. deviation profiles.

When the reference probe is translated in the browsing step 130, the reference profile visualized by the reference probe is updated as described in the paragraph detailing the browsing step 130. In addition, all profiles determined on the basis of the reference profile are also updated according to the updated reference profile.

In the preferred embodiment, when the reference probe is de-referenced in the setting step 110, all profiles determined on the basis of the reference profile become default profiles.

In a further embodiment of the method 100 according to the invention, the method 100 further comprises an annotating step 145 for annotating a view rendered from the related image data with the profile. This may be the final step of probing. By using one or more flags one can easily annotate regions of the object, which contain suspicious profiles. In clinical practice, this step is important for transmitting the diagnosis from inspecting radiologist to the orthopedist, for example, who performs the arthroscopy. This can be achieved in an efficient way by highlighting the damaged regions of the object in conjunction with the anatomical context. The profiles annotating the view rendered from the related image data at selected locations of the probe on the surface of the object may be stored in a file created or appended in the annotating step 145 for future reference.

The skilled person will appreciate the fact that the method 100 of the current invention may be useful also for non-medical applications comprising, but not limited to, cell morphology, materials science, and geology. For example, the method may be applied to probe the Earth's crust for determining the profile of local density across geological layers at a particular geographical location.

The order of steps in the described embodiments of the method of the current invention is not mandatory, the skilled person may change the order of some steps or perform some steps concurrently using threading models, multi-processor systems or multiple processes without departing from the concept as intended by the present invention. Optionally, two or more steps of the method of the current invention may be combined into one step. Optionally, a step of the method 100 of the current invention may be split into a plurality of steps.

The method 100, such as the one shown in FIG. 1, of the invention can be implemented as a computer program product and can be stored on any suitable medium such as, for example, magnetic tape, magnetic disk, or optical disk. This computer program can be loaded into a computer arrangement comprising a processing unit and a memory. The computer program product, after being loaded, provides the processing unit with the capability to carry out the steps of the method 100.

FIG. 8 schematically shows an embodiment of the system 800 for probing a data of interest on the basis of an object comprised in a related image data, the system comprising:
  an instantiating unit 805 for instantiating a probe;
  a setting unit 810 for setting a parameter of the probe;
  an applying unit 815 for applying the probe to a location on a surface of the object; and
  a determining unit 820 for determining a profile from the data of interest on the basis of the location of the probe;
  a visualizing unit 825 for visualizing the profile;
  a browsing unit 830 for browsing the data of interest;
  a selecting unit 835 for selecting the probe;
  a destroying unit 840 for destroying the probe;
  an annotating unit 845 for annotating a view rendered from the related image data with the profile;
  a user interface 865 for communicating with the system 800.

In the embodiment of the system 800 shown in FIG. 8, there are three input connectors 881, 882 and 883 for the incoming data. The first input connector 881 is arranged to receive data coming in from data storage such as a hard disk, a magnetic tape, flash memory, or an optical disk. The second input connector 882 is arranged to receive data coming in from a user input device such as, but not limited to, a mouse or a touch screen. The third input connector 883 is arranged to receive data coming in from a user input device such as a keyboard. The input connectors 881, 882 and 883 are connected to an input control unit 880.

In the embodiment of the system 800 shown in FIG. 8, there are two output connectors 891 and 892 for the outgoing data. The first output connector 891 is arranged to output the data to data storage such as a hard disk, a magnetic tape, flash memory, or an optical disk. The second output connector 892 is arranged to output the data to a display device. The output connectors 891 and 892 receive the respective data via an output control unit 890.

The skilled person will understand that there are many ways to connect input devices to the input connectors 881, 882 and 883 and the output devices to the output connectors 891 and 892 of the system 800. These ways comprise, but are not limited to, a wired and a wireless connection, a digital network such as a Local Area Network (LAN) and a Wide Area Network (WAN), the Internet, a digital telephone network, and an analogue telephone network.

In an embodiment of the system 800 according to the invention, the system 800 comprises a memory unit 870. The system 800 is arranged to receive an input data from external devices via any of the input connectors 881, 882, and 883 and to store the received input data in the memory unit 870. Loading the data into the memory unit 870 allows a quick access to relevant data portions by the units of the system 800. The input data may comprise the data of interest and the related image data. The memory unit 870 may be implemented by devices such as a Random Access Memory (RAM) chip, a Read Only Memory (ROM) chip, and/or a hard disk. Preferably, the memory unit 870 comprises a RAM for storing the data of interest and the related image data. The memory unit 870 is also arranged to receive data from and to deliver data to the units of the system 800 comprising the instantiating unit 805, the setting unit 810, the applying unit 815, the determining unit 820, the visualizing unit 825, the browsing unit 830, the selecting unit 835, the destroying unit 840, the annotating unit 845, and the user interface 865 via the memory bus 875. The memory unit 870 is further arranged to make the data available to external devices via any of the output connectors 891 and 892. Storing the data from the units of the system 800 in the memory unit 870 advantageously improves the performance of the units of the system 800 as well as the rate of transfer of data from the units of the system 800 to external devices.

Alternatively, the system 800 does not comprise the memory unit 870 and the memory bus 875. The input data used by the system 800 is supplied by at least one external device, such as external memory or a processor, connected to the units of the system 800. Similarly, the output data produced by the system 800 is supplied to at least one external device, such as external memory or a processor, connected to the units of the system 800. The units of the system 800 are arranged to receive the data from each other via internal connections or via a data bus.

In a further embodiment of the system 800 according to the invention, the system 800 comprises a user interface 865 for communicating with the system 800. The user interface 865 may comprise a display unit for displaying data to the user and a selection unit for making selections. Combining the system 800 with a user interface 865 allows the user to communicate with the system 800. The user interface 865 is arranged to display views rendered from the related image data to the user. The user interface 865 may be further arranged to display the probe and a UI window for setting and checking parameters of the probe. Optionally, the user interface may comprise a plurality of modes of operation of the system 800 such as a mode for using a particular visualizing method. The skilled person will understand that more functions can be advantageously implemented in the user interface 865 of the system 800.

Alternatively, the system may employ an external input device and/or an external display connected to the system 800 via the input connectors 882 and/or 883 and the output connector 892. The skilled person will also understand that there exist many user interfaces that can be advantageously comprised in the system 800 of the current invention.

The system 800, such as the one shown in FIG. 8, of the invention can be implemented as a computer program product and can be stored on any suitable medium such as, for example, magnetic tape, magnetic disk, or optical disk. This computer program can be loaded into a computer arrangement comprising a processing unit and a memory. The computer program product, after being loaded, provides the processing unit with the capability to carry out the assigned tasks.

FIG. 9 schematically shows an embodiment of the image acquisition apparatus 900 employing the system 800 of the invention, said image acquisition apparatus 900 comprising an image acquisition apparatus unit 910 connected via an internal connection with the system 800, an input connector 901, and an output connector 902. This arrangement advantageously increases the capabilities of the image acquisition apparatus 900 providing said image acquisition apparatus 900 with advantageous probing and visualizing capabilities of the system 800. Examples of image acquisition apparatus comprise, but are not limited to, a CT system, an X-ray system, an MRI system, an US system, a PET system, and a SPECT system.

FIG. 10 schematically shows an embodiment of a workstation 1000. The system comprises a system bus 1001. A processor 1010, a memory 1020, a disk input/output (I/O) adapter 1030, and a user interface (UI) 1040 are operatively connected to the system bus 1001. A disk storage device 1031 is operatively coupled to the disk I/O adapter 1030. A keyboard 1041, a mouse 1042, and a display 1043 are operatively coupled to the UI 1040. The system 800 of the invention, implemented as a computer program, is stored in the disk storage device 1031. The workstation 1000 is arranged to load the program and input data into memory 1020 and execute the program on the processor 1010. The user can input information to the workstation 1000 using the keyboard 1041 and/or the mouse 1042. The workstation is arranged to output information to the display device 1043 and/or to the disk 1031. The skilled person will understand that there are numerous other embodiments of the workstation known in the art and that the present embodiment serves the purpose of illustrating the invention and must not be interpreted as limiting the invention to this particular embodiment.

It should be noted that the above-mentioned embodiments illustrate rather than limit the invention and that those skilled in the art will be able to design alternative embodiments without departing from the scope of the appended claims. In the claims, any reference signs placed between parentheses shall not be construed as limiting the claim. The word "comprising" does not exclude the presence of elements or steps not listed in a claim. The word "a" or "an" preceding an element does not exclude the presence of a plurality of such elements. The invention can be implemented by means of hardware comprising several distinct elements and by means of a suitable programmed computer. In the system claims enumerating several units, several of these units can be embodied by one and the same item of hardware or software. The usage of the words first, second and third, etcetera does not indicate any ordering. These words are to be interpreted as names.

The invention claimed is:

1. A method of probing data of interest on a basis of an object comprised in a related image data, the method comprising:
   acquiring, with an image acquisition apparatus unit, the related image data representing the object;
   rendering, on an associated display, an image of the object from the related image data;
   with a processor, instantiating a probe in the displayed image;
   applying the probe to a location on a surface of the object in the displayed image; and
   determining, with the processor, a profile from the data of interest associated with the object on a basis of the location of the probe relative to the surface of the object in the displayed image.

2. The method as claimed in claim 1 wherein the profile represents a property of the object along at least one trajectory extending into the object from the location on the surface of the object.

3. The method as claimed in claim 2 further including with the probe defining:
   a direction of the trajectory;
   a depth of the trajectory; and/or a plurality of trajectories.

4. The method as claimed in claim 3 further comprising visualizing the profile on the associated display.

5. The method as claimed in claim 4 wherein the probe comprises a flag on which a graph depicting the property of the object vs depth below the surface of the object.

6. The method as claimed in claim 4 wherein the probe defines a plurality of parallel trajectories arranged in a line to define a cutting plane for visualizing a cross section of the object.

7. The method as claimed in claim 2 further comprising moving the probe along the surface of the object in the displayed image for browsing the property along trajectories from different locations on the object.

8. The method as claimed in claim 4 further comprising rotating the probe to rotate the cutting plane.

9. The method as claimed in claim 1, further comprising:
   applying a second probe to a second location on the surface of the object in the displayed image; and
   determining a second profile on the basis of the second location.

10. The method as claimed in claim 1 further comprising;
    annotating the probe;
    storing the image and the annotated probe;
    displaying the stored image in association with the annotated probe.

11. A non-transitory computer-readable medium carrying computer code that, when executed by a computer, controls the computer to perform the method of claim 1.

12. The method of claim 1, wherein the related image data is magnetic resonance imaging data, computed tomography data, X-ray data, ultrasound data, positron emission tomography data, or single photon emission computed tomography data.

13. The method as claimed in claim 1, wherein the object is an internal anatomical organ or structure.

14. A system for probing properties of an object, the system comprising:
    a display device;
    a user input device:
    a processor configured to:
      receive image data corresponding to the object,
      render an image of the object from the image data on the display device,
      render a probe on the image displayed on the display,
      under control of the user input device, move the probe to designate a location on surface the object displayed in the rendered image, and
      determine a profile depicting interior properties of the object adjacent to the location on the object designated by the probe.

15. The system as claimed in claim 14, wherein the profile represents the property of the object along at least one trajectory extending into an interior of the object.

16. The system as claimed in claim 15, wherein the processor is further configured to:
    render the probe with a display field; and
    render a graphical display of the property vs distance along the trajectory In the display field of the rendered probe.

17. The system as claimed in claim 16, further including:
    at least one of an MRI system, a CT system, an X-ray system, an ultrasound system, a PET system, or a SPECT system which acquires the image data.

18. An apparatus for probing interior properties of an anatomical object, the apparatus comprising:
    a display device which displays rendered images of at least the anatomical object;
    a processor configured to:
      receive input data acquired by a diagnostic imaging apparatus,
      reconstruct the image rendered on the display device from the input data,
      instantiate a probe on a location on a surface of the displayed anatomical object on the display device, and
      generate a profile indicative of properties interior of the object adjacent to the location of the probe based upon the input data in a visual representation rendered on the display device proximate to the location designated by the probe; and
    a user input device by Which the processor is controlled to position the probe on a location of interest.

19. The apparatus as claimed in Claim 18, wherein the generated profile is indicative of at least one of a relaxation time information, dielectric polarizability infomation, magnetic susceptibility information, local density information, a local concentration of an element a local concentration of a chemical compound, or a Hounsfield value.

20. The apparatus as claimed in claim 18, wherein the profile is indicative of the property along one or more trajectories extending into an interior of the object in one or more directories specified by the probe.

* * * * *